(12) United States Patent
Oh et al.

(10) Patent No.: US 11,447,733 B2
(45) Date of Patent: Sep. 20, 2022

(54) TRANSPARENT DISC-SHAPED MICROPARTICLES COATED WITH POLYDOPAMINE

(71) Applicant: UNIVERSITY-INDUSTRY COOPERATION GROUP OF KYUNG HEE UNIVERSITY, Yongin-si (KR)

(72) Inventors: Tong In Oh, Hwaseong-si (KR); Sung Hyun Kim, Iksan-si (KR); Wook Park, Yongin-si (KR); Eun Ah Lee, Seoul (KR)

(73) Assignee: UNIVERSITY-INDUSTRY COOPERATION GROUP OF KYUNG HEE UNIVERSITY, Yongin-si (KR)

( * ) Notice: Subject to any disclaimer, the term of this patent is extended or adjusted under 35 U.S.C. 154(b) by 258 days.

(21) Appl. No.: 16/486,600

(22) PCT Filed: Jan. 15, 2018

(86) PCT No.: PCT/KR2018/000652
§ 371 (c)(1),
(2) Date: Aug. 16, 2019

(87) PCT Pub. No.: WO2018/151423
PCT Pub. Date: Aug. 23, 2018

(65) Prior Publication Data
US 2020/0231919 A1 Jul. 23, 2020

(30) Foreign Application Priority Data
Feb. 17, 2017 (KR) .......................... 10-2017-0021375

(51) Int. Cl.
C12M 1/12 (2006.01)
C12M 1/00 (2006.01)
C12N 11/089 (2020.01)

(52) U.S. Cl.
CPC ............ *C12M 25/16* (2013.01); *C12M 23/20* (2013.01); *C12N 11/089* (2020.01); *C12N 2533/30* (2013.01)

(58) Field of Classification Search
CPC .. C12N 11/08; C12N 5/0068; C12N 2537/10; C12N 2533/30; C12M 23/20; C12M 25/16
See application file for complete search history.

(56) References Cited

U.S. PATENT DOCUMENTS 5,573,934 A * 11/1996 Hubbell ............... A61K 9/1647
424/463
2011/0053783 A1 3/2011 Du et al.
(Continued)

FOREIGN PATENT DOCUMENTS

JP 2011-115604 A 6/2011
JP 2014-64572 A 4/2014
(Continued)

OTHER PUBLICATIONS

Yamada et al. Cell-sized condensed collagen microparticles for preparing microengineered composite spheroids of primary hepatocytes. Lab on a Chip (2015), 15, 3941-3951. (Year: 2015).*
(Continued)

*Primary Examiner* — Sean C. Barron
(74) *Attorney, Agent, or Firm* — Sughrue Mion, PLLC

(57) ABSTRACT

The present invention relates to transparent disc-shaped microparticles having polydopamine-modified surfaces and cell culture using the same. When the disc-shaped microparticles coated with polydopamine according to the present
(Continued)

invention are used in cell culture, cell adhesive properties are improved and an inverted microscope may be employed to observe cells, which are major advantages when compared to conventional spherical microcarriers.

4 Claims, 6 Drawing Sheets

(56) References Cited

U.S. PATENT DOCUMENTS

2014/0228252 A1* 8/2014 Kwon ................ G01N 33/5434
                                                                506/16
2016/0346217 A1    12/2016 White et al.

FOREIGN PATENT DOCUMENTS

| KR | 10-0871652 B1 | 12/2008 |
| KR | 10-2011-0134790 A | 12/2011 |
| KR | 10-2014-0063480 A | 5/2014 |
| KR | 10-2015-0118248 A | 10/2015 |
| KR | 10-2015-0141165 A | 12/2015 |

OTHER PUBLICATIONS

Chuah et al. Simple surface engineering of polydimethylsiloxane with polydopamine for stabilized mesenchymal stem cell adhesion. (Scientific Reports (2015), 5(18162), 12 pages. (Year: 2015).*
Office Action for corresponding KR 10-2017-0021375, dated Nov. 20, 2018.
International Search Report for PCT/KR2018/000652, dated May 16, 2018.

* cited by examiner

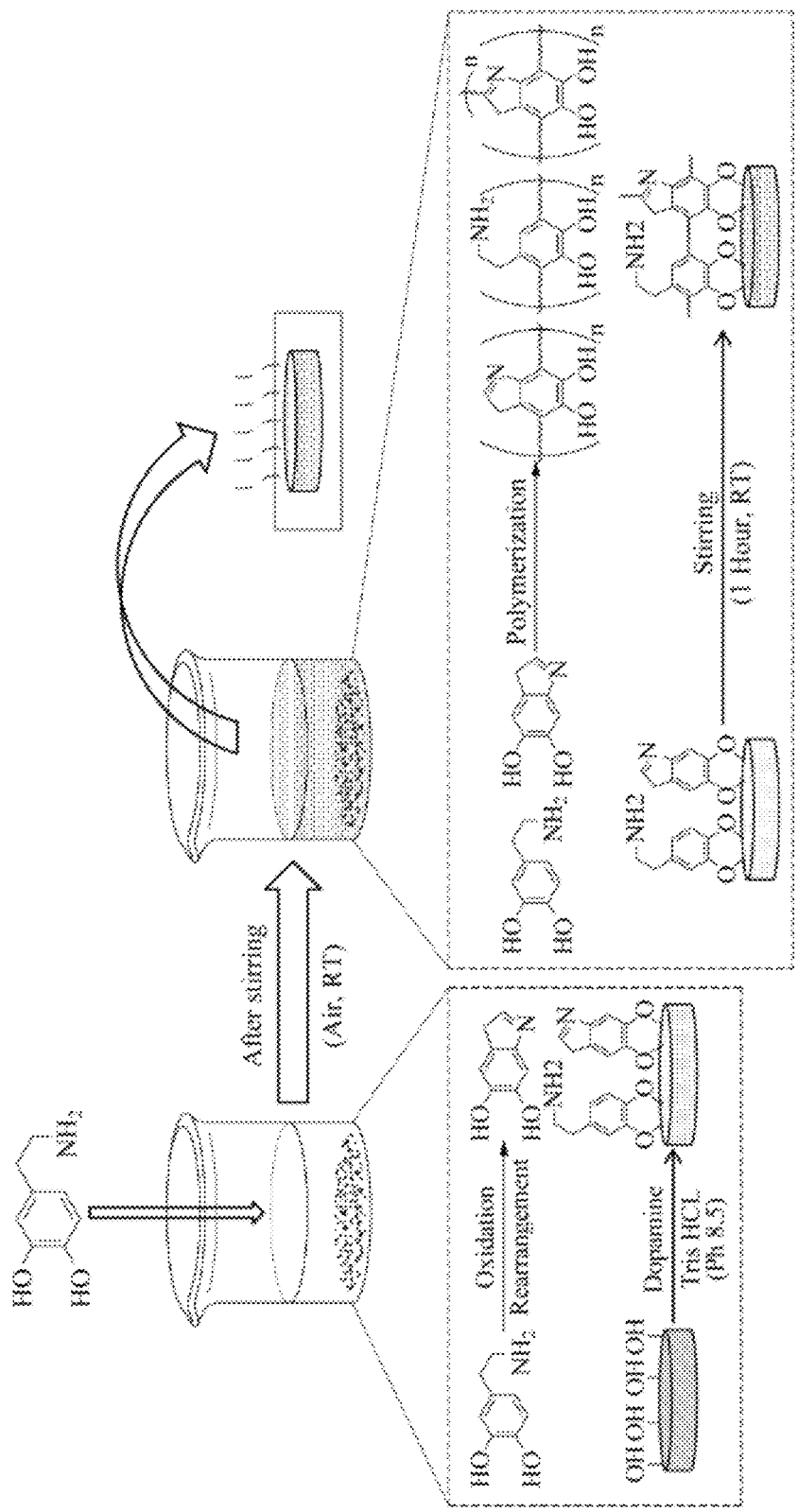
[FIG. 1]

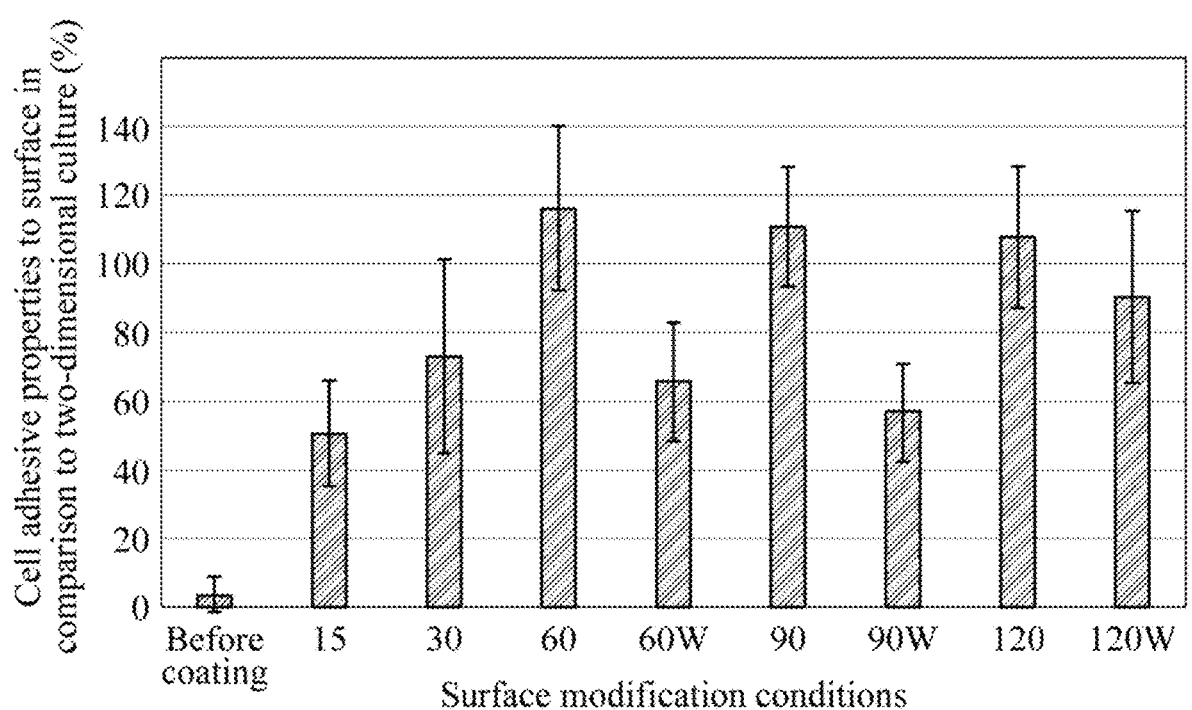
[FIG. 2]

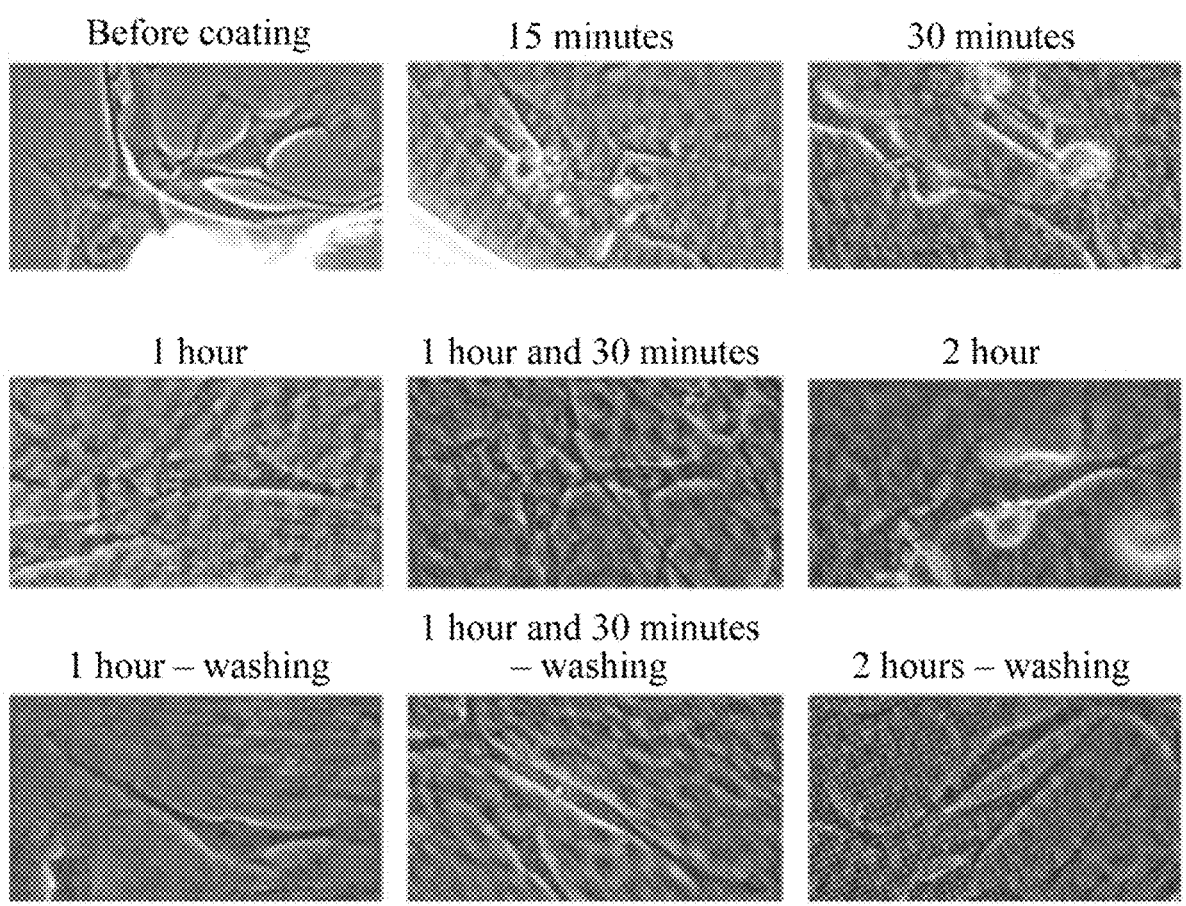
[FIG. 3]

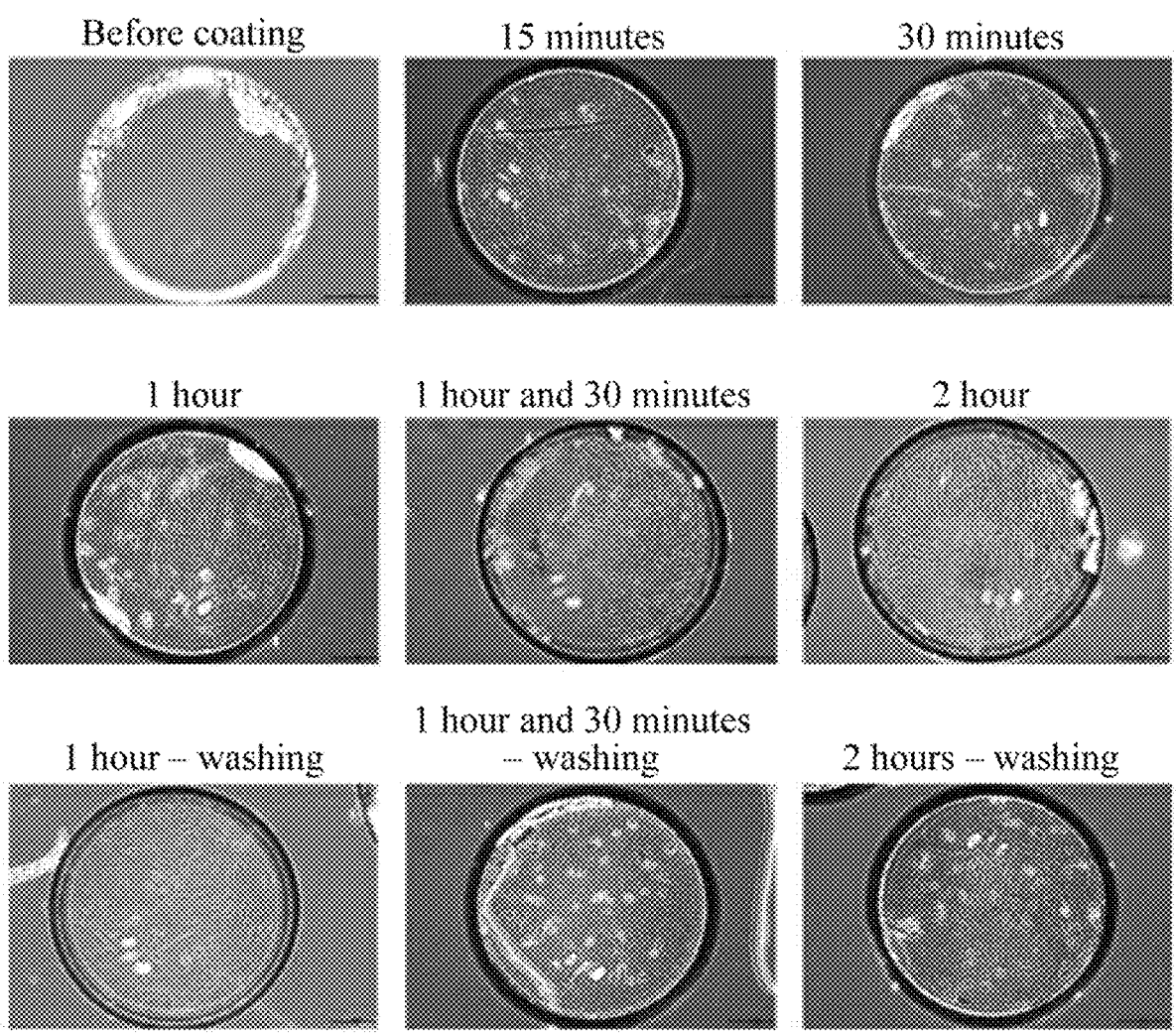
[FIG. 4]

[FIG. 5]
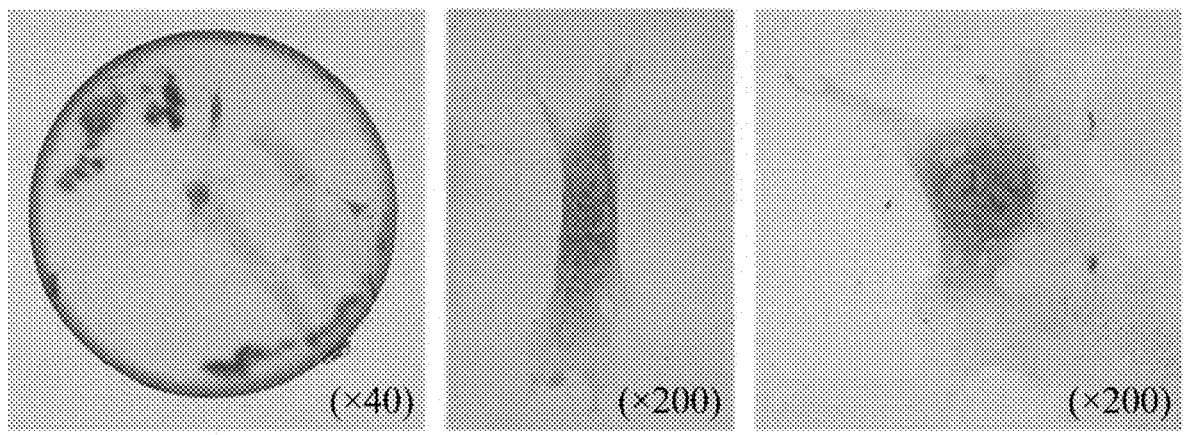

[FIG. 6]
| Before coating | 15 minutes | 30 minutes |
|---|---|---|
| 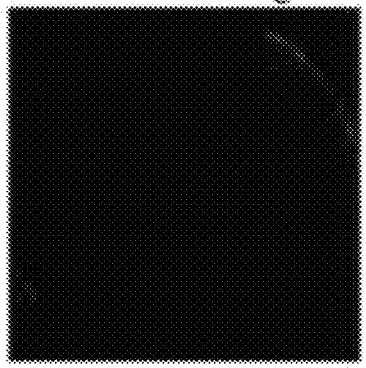 | 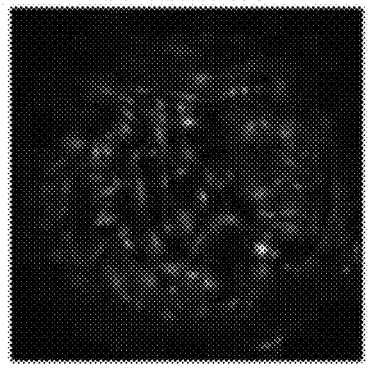 | 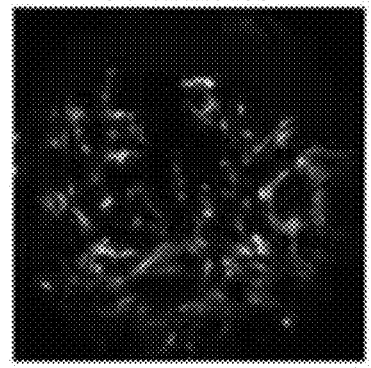 |
| 1 hour | 1 hour and 30 minutes | 2 hour |
| 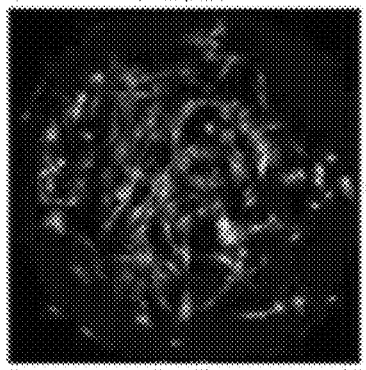 | 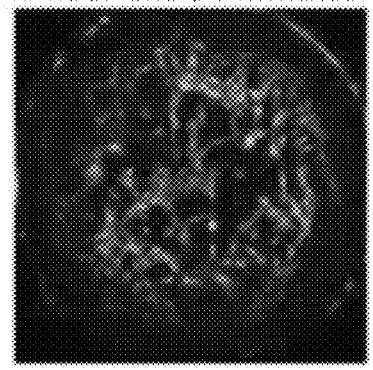 | 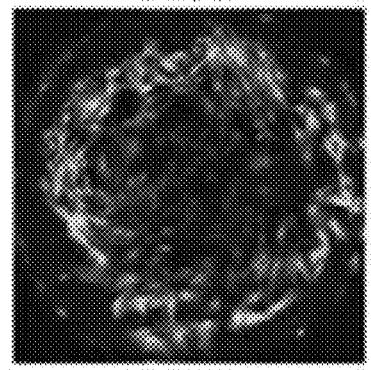 |
| 1 hour — washing | 1 hour and 30 minutes — washing | 2 hours — washing |
| 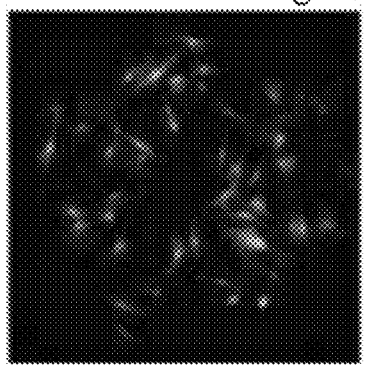 | 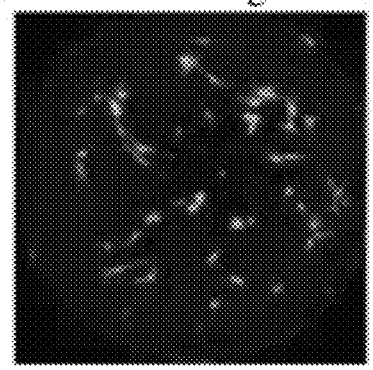 | 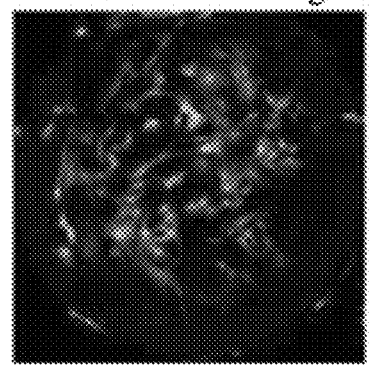 |

TRANSPARENT DISC-SHAPED MICROPARTICLES COATED WITH POLYDOPAMINE

CROSS-REFERENCE TO RELATED APPLICATION

This application is a National Stage of International Application No. PCT/KR2018/000652, filed on Jan. 15, 2018, which claims priority to Korean Patent Application No. 10-2017-0021375, filed on Feb. 17, 2017 in the Korean Intellectual Property Office, the disclosure of which is incorporated herein by reference.

TECHNICAL FIELD

The present invention relates to transparent disc-shaped microparticles having polydopamine-modified surfaces and cell culture using the same.

BACKGROUND ART

The purpose of culturing animal cells is to produce various kinds of medical products including enzymes, hormones, vaccines, immunomodulators, anti-cancer drugs, exosomes, and cell therapeutic agents for treating diseases.

Animal cell culture method involves providing artificial in vivo-like environment for in vitro cell expansion. For some animal cells such as hybridoma or leukemia cell lines, scale-up expansion can be easily proceeded because they can be maintained by suspension culture. However, most of animal cells are adherent cells and they need surface to make attachment for in vitro expansion.

Since large number of stem/progenitor cells are needed for regenerative medicine and the related research, various scale-up manufacturing methods were developed to meet the need. Specifically, to increase cell yield per unit volume, area of cell-adherent surface was maximized by systems such as a microfiber, a hollow fiber, a ceramic matrix, or the like.

The microcarrier-based three-dimensional culture method was developed to overcome the limitations of conventional two-dimensional culture not only in volume efficiency but also in the way of handling. However, because the surface of microcarriers have three-dimensional contour, it is not easy to monitor the cell density or cell morphology.

The present invention provide an unique 3 dimensional culture method that can realize advantages of both the three-dimensional and two-dimensional culture by increasing surface efficiency and making two-dimensional cell observation possible at the same time.

A disc-shaped microparticle was prepared by photo-polymerizing a mixture of a photocurable synthetic polymer and linker molecules having a functional group that can be polymerized with photocurable substance and an alkoxysilyl group and the microparticle surface was coated with polydopamine to provide excellent cell adhesive properties and easy observation.

DISCLOSURE

Technical Problem

The present invention has been made in view of the above problems, and it is one object of the present invention to provide a microparticle having a two-dimensional plane formed by polymerization of a photocurable substance and a polydopamine-coated layer. The microparticles according to the present invention allow easy observation of cell morphology and density of attached cells while permitting three-dimensional culture.

Technical Solution

In accordance with one aspect of the present invention, provided is a disc-shaped microparticle for cell culture, including a polydopamine-coated surface layer, wherein the disc-shaped microparticle is formed by photocuring polymerization of a photocurable substance having an acrylate functional group and a linker having a functional group polymerizable with the photocurable substance and an alkoxysilyl group.

In accordance with another aspect of the present invention, provided is a method of preparing disc-shaped microparticles for cell culture having polydopamine-coated surfaces, the method including a) a step of preparing microparticles by photocuring polymerization of a mixture of a photocurable substance and a linker having a functional group polymerizable with the photocurable substance and an alkoxysilyl group; and (b) a step of adding a dopamine hydrochloride solution to the microparticles and stirring.

According to the present invention, the disc-shaped microparticle may include a coded polymeric microparticle core and a silica shell, wherein a carboxyl group or an amine group may be introduced to the surface of the silica shell.

According to the present invention, the disc-shaped microparticles may improve cell adhesive properties during cell culture, and may allow cell observation with an inverted microscope during cell culture, thus enabling easy observation.

According to the present invention, the stirring in the step of (b) may be performed for 40 to 80 minutes.

Advantageous Effects

When the disc-shaped microparticles coated with polydopamine according to the present invention are used in cell culture, cell adhesive properties are improved and an inverted microscope can be employed in a same way to observe cells in two-dimensional culture, which are major advantages when compared to conventional spherical microparticles.

DESCRIPTION OF DRAWINGS

FIG. 1 illustrates a process for modifying the surfaces of transparent disc-shaped microparticles with polydopamine by photocuring.

FIG. 2 shows the result of evaluating cell adhesive properties of polydopamine-coated microparticles.

FIG. 3 shows the result of observing morphology of cells attached to the surfaces of polydopamine-coated microparticles.

FIG. 4 shows the result of observing morphology and density of cells attached to the surfaces of polydopamine-coated microparticles.

FIG. 5 shows the result of analyzing optical morphology of cells attached to polydopamine-coated microparticles using methyl violet.

FIG. 6 shows the result of observing GFP expressed on the surfaces of cells attached to polydopamine-coated microparticles using a confocal microscope.

BEST MODE

Hereinafter, the present invention will be described in more detail with reference to the following examples. Those skilled in the art will appreciate that these examples are provided for illustrative purposes only and should not be construed as limiting the scope and spirit of the present invention.

The present invention relates to a transparent disc-shaped microparticle having a polydopamine-modified surface and cell culture using the same. According to an embodiment of the present invention, for scale-up manufacturing of adherent cells, the disc-shaped microparticles may be used for a three-dimensional culture system in which cells are attached to micrometer-sized microparticles and cultured.

According to an embodiment of the present invention, the disc-shaped microparticle for cell culture may include a microparticle and a polydopamine layer formed on the surface of the microparticle. In particular, according to an embodiment of the present invention, the disc-shaped microparticle for cell culture may have a polydopamine-modified surface.

The disc-shaped microparticle may take the form of a round tray-shaped disc having a flat top surface and may be transparent.

In particular, since the disc-shaped microparticle is disc-shaped, unlike conventional microcarriers having spherical shapes, the disc-shaped microparticle may include two two-dimensional planes. In addition, observation and analysis methods used for two-dimensional culture may be applied due to transparency of the disc-shaped microparticle.

The disc-shaped microparticles may be formed by photocuring polymerization using a mixture of a photocurable substance and a linker. The photocurable substance may include an acrylate functional group, and the linker may include a functional group polymerizable with the photocurable substance and an alkoxysilyl group.

A photocurable substance is a substance that is cured upon irradiation with light. When the photocurable substance is irradiated with light, structural changes occur, and curing of a substance through cross-linking is a typical example.

For example, ethoxylated trimethylol propane triacrylate, 2-hydroxyethyl methacrylate, methylmethacrylate, acrylamide, allylamine, polyethylene oxide, polyethyleneglycol diacrylate, polypropylene glycol diacrylate, polyurethane acrylate, polyvinyl pyrrolidone, polyvinyl alcohol, polyacrylate and combinations thereof may be used as a photocurable substance.

Among various photocurable substances, in the case of an acrylate-based photocurable substance, radicals are formed by a polymerization initiator in a photoreaction, and subsequently a continuous curing reaction occurs by free radical-initiated polymerization through reaction with an alkenyl group in an acrylate. The acrylate-based photocurable substance has a wide range of applications because the substance may be cured at a high rate and physical properties thereof can be variously controlled depending on oligomer type and number of acrylate groups.

For example, vinyl-based functional groups such as vinyl chloride, vinyl bromide, vinyl alcohol, vinyl ester, vinylacetate, vinyl epoxide, vinyl amide, and vinyl cyanide and combinations thereof may be used as a functional group for radical polymerization of a photocurable substance.

When a vinyl-based functional group is used, electron density at a beta carbon varies depending on the polarity of a functional group attached to the alpha carbon of a vinyl group, a difference in radical polymerization reactivity of a photocurable substance occurs, and various physical properties are observed as a result of photocuring.

For example, in the case of vinyl ester, the strong polarity of the carbonyl group of a functional group generally attracts electrons of an electron-rich vinyl group to generate an electron-deficient beta carbon, and promotes polymerization of a photocurable substance. Such an increase in electrophilic property may increase reactivity with a thiol group, an amine group or the like, which is capable of binding with an acrylate.

An alkoxysilyl group is a functional group in which silane has 1 to 3 oxygen atoms and an alkyl group is bonded as a linker, and is named alkoxy (in the case of one oxygen atom), dialkoxy (in the case of two oxygen atoms), and trialkoxysilyl (in the case of three oxygen atoms), depending on the number of oxygen atoms.

The alkoxysilyl group acts as a protective group to prevent the influence of oxygen molecules in the air during photocuring of an acrylate. The alkoxysilyl group may form a silicon-oxide bond through hydrolysis and a condensation reaction with a hydroxyl group or an alkoxysilyl group, and may form crosslink through an ester exchange reaction with a hydroxyl group.

According to an embodiment of the present invention, the disc-shaped microparticle for cell culture may include a coded polymeric microparticle core and a silica shell surrounding the core.

The polymeric microparticle core may be coded in a variety of known ways and may include, for example, a graphical code, a fluorescent code or a color code. In addition, the polymer constituting the polymeric microparticle core is preferably a photocurable polymer in that the polymer may be variously patterned by optical lithography.

The photocurable polymer may mainly contain an acrylic photocurable substance. In addition to the acrylic photocurable substance, the photocurable polymer may be mixed with a linker substance having both a functional group capable of reacting with the photocurable substance to enable photocuring and a functional group capable of forming silica.

The polymer microparticle core formed by photocuring may be disc-shaped, and the size of the core may range from several micrometers to several millimeters. For example, the polymeric microparticle core may be prepared to a thickness ranging from several micrometers to several hundred micrometers, and the diameter of the core may range from several tens of micrometers to several millimeters.

The silica shell may surround and protect the polymeric microparticle core, thereby preventing foreign matter absorption into the polymer of microparticle core enabling prevention of analysis errors.

The silica shell may provide the chemical and mechanical stability of the coded polymeric microparticles to help the microparticles be used in a variety of environments and solutions. The silica shell may provide chemical and mechanical stability to the coded polymeric microparticles so that the microparticles may be used in a variety of environments and solutions.

The coded polymeric microparticle core and the silica shell may be linked by a —Si—O—Si— bond, so that a stable structure may be formed by strong chemical bonding between the core and the shell. Due to the presence of the silica shell, the surface of the polymer microparticle may have low binding properties to unspecified materials while enhancing binding properties to biomaterials.

In addition, a functional group such as a carboxyl group or an amine group may be introduced into the surface of the silica shell. By introducing the functional group, the surface of the silica shell is modified and may be used for cell culture. That is, according to the present invention, since the silica shell surfaces of the microparticles are modified with a carboxyl group or an amine group, the microparticles may exhibit excellent cell adhesive properties.

Furthermore, a carboxyl group or an amine group may be introduced to the surface of the silica shell to covalently bind to various biomolecules widely used in the field of biomedical or clinical diagnosis. For example, when the surface of the silica shell is modified with a carboxyl group or an amine group, any one of biomaterials selected from the group consisting of an antigen, an antibody, DNA, RNA, and an oligonucleotide may be introduced into the microparticles according to the present invention.

According to the present invention, the linker may react with a photocurable substance to form a copolymer while forming a skeleton of the microparticles, and at the same time, an alkoxysilyl group may be grafted on the surface of the coded polymer microparticle core.

When the microparticles are prepared only from a photocurable substance, the formation of a silica shell by silica coating in the next step may be not easy. On the other hand, when a linker having both a functional group capable of polymerization with a photocurable substance and an alkoxysilyl group is mixed with the photocurable substance to form a mixture and cured, a silica shell may be coated through alkoxysilyl groups grafted to the surfaces of polymeric microparticle cores.

For example, the linker may be a compound represented by Formula 1 below.

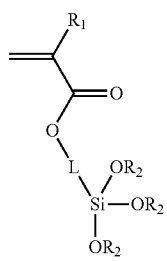

Formula 1

In Formula 1, $R_1$ may be hydrogen, methyl or ethyl, and R 2 may be a $C_1$ to $C_8$ linear or branched alkyl. In addition, L may be an alkylene or arylene having $C_1$ to $C_{12}$ or a structure in which the alkylene and the arylene are arbitrarily connected. In particular, Formula 1 may be 3-(trimethoxysilyl)propylacrylate (TMSPA).

According to the present invention, the polydopamine layer may be formed on the surface of the microparticle, and may modify the surface of the microparticle. The polydopamine layer may be composed of polydopamine (PDA), and the dopamine is represented by Formula 2 below.

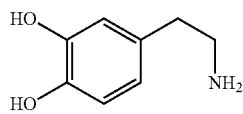

Formula 2

According to an embodiment of the present invention, disc-shaped microparticles having polydopamine-modified surfaces may exhibit excellent cell adhesive properties when applied to cell culture. In particular, to apply the microparticles formed through photocuring to three-dimensional cell culture, the surfaces of the microparticles may be modified using polydodamine to facilitate cell adhesion on the surfaces.

FIG. 1 illustrates a process for modifying the surfaces of transparent disc-shaped microparticles with polydopamine by photocuring.

Referring to FIG. 1, a method of modifying the surfaces of the disc-shaped microparticles by photocuring using polydopamine is described below.

A precursor of dopamine hydrochloride is dissolved in a 10 mM Tris hydrochloric acid (Tris/HCl) buffer solution (pH=8.5) and transparent disc-shaped microparticles are added to the solution. Then, the solution containing microparticles is stirred at room temperature (RT).

Dopamine forms polydopamine on the surfaces of the microparticles through self-oxidative polymerization based on the reducing power of the catechol group of dopamine (acting as an oxidative polymerization initiator). The interaction of tris(hydroxymethyl)aminomethane and dopamine present in the buffer solution also serves as a catalyst for the oxidative polymerization. The hydroxyl group of dopamine interacts with the hydrophilic group of the disc-shaped microparticle to have surface adhesive properties.

In particular, in the oxidation process of dopamine, dopamine quinone is formed through oxidation, and 5,6-dihydroxyindole is formed through a nucleophilic ring-forming reaction of the amine group of dopamine. Through the covalent polymerization and physical interaction of the 5,6-dihydroxyindole formed in the oxidation process, polydopamine is formed and the surfaces of the microparticles are modified with polydopamine.

That is, a component derived from mussel adhesive protein, polydopamine, has cell compatibility and has strong surface adhesive properties even in an aqueous solution. Therefore, as a result of modifying the surfaces of the disc-shaped microparticles using polydodamine, when cells are cultured on the surfaces of the disc-shaped microparticles in a culture medium, cell adhesive properties are increased.

In addition, in the process of expanding cell culture after cell attachment, it is necessary to observe the density and morphology of cells to determine the degree of cell growth and the time of subculture. With conventional spherical microcarriers used in three-dimensional culture, it is difficult to observe the density and shape of cells due to its three-dimensional shape. However, when the disc-shaped microparticles having polydopamine-modified surfaces according to an embodiment of the present invention are used in cell culture, cells may be observed using an inverted microscope, allowing monitoring and analysis of the state and function of cells. In this regard, the disc-shaped microparticles have significant advantages over the conventional spherical microparticles.

Now, the present invention will be described in more detail with reference to the following preferred examples. These examples are provided for illustrative purposes only and should not be construed as limiting the scope and spirit of the present invention.

Example 1: Preparation of Microparticles by Photocuring and Modification of Surfaces of Microparticles Using Polydopamine The basic skeletal structure of microparticles was prepared using a mixture of a photocurable substance and a linker having a functional group polymerizable with the photocurable substance, alkoxy and a silyl group.

In preparing the microparticles, a spacer for adjusting height was placed on a substrate, the mixture was injected, the substrate was covered with a transparent substrate, and the assembled substrate was firmly fixed so as not to separate. At this time, the height of hydrogel particles was determined by the height of the spacer, and a mask designed in a desired shape was placed on the surface of the transparent substrate, and the mask was irradiated with parallel light to selectively transmit light, thereby forming microparticles of a desired shape. The thickness of the microparticles may be in the range of 5 to 300 μm, and the diameter of the particles may be in the range of 50 to 3,000 μm.

According to Example 1, 630 ml of ethoxytrimethylol propane triacrylate as a photocurable substance and 270 ml of 3-(trimethoxysilyl)propylacrylate as a linker were mixed at a volume ratio of 7:3, and then 100 ml of 2-hydroxy-2-methylpropiophenone as an initiator was added to the prepared solution so as to have a 10% volume ratio, and the mixture was used for microparticle preparation.

Acrylate functional groups present at both ends of the photocurable molecules were crosslinked by a free radical polymerization and changed from liquid to solid to form a hydrogel having a three-dimensional shape. Two sizes of microparticles having a thickness (height) of 300 μm and diameters of 500 μm and 1,000 μm, respectively, were prepared through photocuring polymerization.

The microparticles synthesized by photocuring polymerization were added to 50 ml of a Tris hydrochloric acid (Tris/HCl) buffer solution (pH=8.5), a dopamine hydrochloride (DA/HCl) solution at a concentration of 0.6 mg/ml was added thereto, and to proceed a reaction, the mixture was stirred at room temperature for 15 minutes, 30 minutes, 1 hour, 1 hour and 30 minutes, and 2 hours, respectively. After stirring, the mixture was washed with absolute ethanol to stop the reaction, and the mixture was placed in ethanol and stored at room temperature.

As the time to coat with polydopamine increases, the surfaces of the microparticles change to dark brown. Thus, for the purpose of reducing the coloration due to coating, the groups which had been surface-modified with polydopamine for more than 1 hour were subjected to additional washing and compared with non-washed ones as indicated in FIG. 2.

Example 2: Cell Culture Using Surface-Modified Microparticles

Microparticles of various conditions with different degrees of surface modification by polydopamine were placed in a 48 well plate without overlapping each other, and $2 \times 10^4$ cells per well were added thereto and incubated overnight (16 hours) so that approximately 75% of the surfaces of the microparticles were covered with cells.

After the incubation for 16 hours, unattached cells were removed by changing a medium, and the degree of attachment of cells to the surfaces of the microparticles was evaluated by comparing with the number of cells attached per unit area in a general two-dimensional 48-well plate.

FIG. 2 shows the result of evaluating cell adhesive properties of polydopamine-coated microparticles. Referring to FIG. 2, the number of adherent cells cultured on polydopamine-coated microparticles were compared with the number of adherent cells on conventional two-dimensional surfaces. Also, the number of adherent cells on microcarriers coated with polydopamine for different duration were compared to determine best coating condition for cell adhesion.

As shown in FIG. 2, in the groups of microparticles coated with polydopamine for shorter than 1 hour (groups treated with 15 min and 30 min, respectively), exhibited 50% and 72% of cell adhesion, respectively, compared to cells cultured in 2-dimensional surfaces. In a group treated for more than 1 hour, cell adhesiveness was similar to that of cells cultured on the 2-dimensional surfaces.

FIG. 3 shows the result of observing morphology of cells attached to the surfaces of polydopamine-coated microparticles. Referring to FIG. 3, morphology of cells attached to the surfaces of microparticles is compared between groups of microparticles coated for different duration of time to determine best coating condition for observation.

Referring to FIGS. 2 and 3, when polypdopamine coating time increases, cell adhesive properties increase (FIG. 2), but the darkness of the microparticles also increases, resulting in image of cell morphology being obscure (FIG. 3). Thus, after testing the degree of cell adhesion on the microparticles washed after polydopamine coating, it was confirmed that microparticles (60 W, 90 W and 120 W) washed after polydodamine coating showed lower cell adhesive properties (FIG. 2). Based on these observation, it was determined that microparticle coated with polydopamine for 1 hour provided an optimal condition for cell adhesion and observation through inverted microscope.

Example 3: Optical Analysis of Cells Cultured in Surface-Modified Microparticles FIG. 4 shows the result of observing morphology and density of cells attached to the surfaces of polydopamine-coated microparticles.

As shown in FIG. 4, after cell attachment, disc-shaped microparticles were sampled from a culture vessel and the density and morphology of adherent cells in culture were confirmed by an inverted microscope in the same manner as a two-dimensional culture method.

FIG. 5 shows the result of analyzing the optical morphology of cells attached to polydopamine-coated microparticles using methyl violet.

As shown in FIG. 5, optical analysis was proceeded with cells cultured on disc-shaped microparticles after the whole microcarriers were stained with methyl violet. The result shows that observation of cell morphology can be easily performed.

Example 4: Fluorescence Analysis of Cells Cultured on Surface-Modified Microparticles In the case of microparticles used for conventional three-dimensional culture, analysis of cell characteristics involves detachment of the cells from microcarriers with trypsin, and then re-attach to a slide or a coverslip for two-dimensional observation.

In the case of cells attached to the disc-shaped microparticles used in the present invention, the microparticles seeded with green fluorescent protein (GFP)-expressing cells were observed with confocal microscope to evaluate obviousness of observation with fluorescent staining.

FIG. 6 shows the result of observation on GFP-expressing cells attached to polydopamine-coated microparticles using a confocal microscope.

As shown in FIG. 6, the microparticles used for cell culture did not interfere with fluorescence detection, and thus it was confirmed that the surface-modified microparticles according to an embodiment of the present invention may be used for the characterization of cells by on-bead staining without additional passaging on two-dimensional surface.

While the present invention has been particularly shown and described with reference to exemplary embodiments thereof, it will be understood by those of ordinary skill in the art that various changes in form and details may be made therein without departing from the spirit and scope of the present invention.

The invention claimed is:

1. A disc-shaped microparticle for cell culture, comprising a polydopamine-coated surface layer, wherein the disc-shaped microparticle is formed by photocuring polymerization of a photocurable substance having an acrylate functional group and a linker having a functional group polymerizable with the photocurable substance and an alkoxysilyl group,
wherein the disc-shaped microparticle has a thickness of 5 μm to 300 μm and a diameter of 200 μm to 3,000 μm,
wherein the polydopamine-coated surface layer is formed for a time period of 40 to 80 minutes,
wherein the disc-shaped microparticle on which the polydopamine-coated surface layer is formed is configured to be cultured in three dimensions, and a density and shape of cells attached thereto can be observed by an inverted microscope, and
wherein the disc-shaped microparticle for cell culture is optically transparent.

2. The disc-shaped microparticle according to claim 1, wherein the disc-shaped microparticle comprises a coded polymeric microparticle core and a silica shell, wherein a carboxyl group or an amine group is introduced to a surface of the silica shell.

3. A method of preparing disc-shaped microparticles for cell culture having polydopamine-coated surfaces, the method comprising:
(a) a step of preparing microparticles by photocuring polymerization of a mixture of a photocurable substance and a linker having a functional group polymerizable with the photocurable substance and an alkoxysilyl group; and
(b) a step of adding a dopamine hydrochloride solution to the microparticles and stirring,
wherein the stirring of step (b) is performed for a time period of 40 to 80 minutes,
wherein the disc-shaped microparticle has a thickness of 5 μm to 300 μm and a diameter of 200 μm to 3,000 μm,
wherein the disc-shaped microparticle on which the polydopamine-coated surface layer is formed is configured to be cultured in three dimensions, and a density and shape of cells attached thereto can be observed by an inverted microscope, and
wherein the disc-shaped microparticle for cell culture is optically transparent.

4. The method according to claim 3, wherein the disc-shaped microparticle comprises a coded polymeric microparticle core and a silica shell, wherein a carboxyl group or an amine group is introduced to a surface of the silica shell.

* * * * *